United States Patent [19]

Johnson

[11] Patent Number: 4,821,340
[45] Date of Patent: Apr. 18, 1989

[54] FACE SHIELD

[76] Inventor: April E. Johnson, 121 Pleasant St., Marlboro, Mass. 01752

[21] Appl. No.: 153,150

[22] Filed: Feb. 8, 1988

[51] Int. Cl.⁴ ................................................ A61F 9/04
[52] U.S. Cl. .................................................. 2/9; 2/13; 351/158; 128/863
[58] Field of Search .................. 2/13, 9, 206, 173, 174; 351/158; 128/139, 132 R, 201.12, 863

[56] References Cited

U.S. PATENT DOCUMENTS

| | | | |
|---|---|---|---|
| 3,183,523 | 5/1965 | Harrison | 2/13 |
| 3,298,031 | 1/1967 | Morgan | 2/9 |
| 3,298,032 | 1/1967 | Sielisch | 2/13 |
| 3,346,875 | 10/1967 | Weisberger | 2/9 |
| 3,991,753 | 11/1976 | Viesca | 2/9 |

FOREIGN PATENT DOCUMENTS 0860527 10/1952 Fed. Rep. of Germany .............. 2/9

Primary Examiner—Peter Nerbun
Attorney, Agent, or Firm—Blodgett & Blodgett

[57] ABSTRACT

A face shield to protect an individual against inhaling germs and other foreign bodies comprising a permanent clip portion which is adapted to be mounted on the nose piece of a pair of eyeglasses and a disposable sheet of relatively thin rigid plastic which is removably attached to the clip. This enables the sheet to be removed and discarded after a single use and replaced by an identical sheet prior to treatment of a new patient.

10 Claims, 2 Drawing Sheets

FACE SHIELD

BACKGROUND OF THE INVENTION

The present invention relates generally to devices for protecting an individual against inhaling germs and foreign bodies. Surgical masks have been used recently for many years for protecting patients as well as medical personnel. However, the masks have many disadvantages; they press against the head of the individual and are uncomfortable to wear. Breathing is difficult and the masks are unreliable because of their porous nature.

The above problems have been addressed by the developments of shields of clear rigid plastic material which are adapted to be mounted on a pair of eyeglasses. The shield lies in front of the nose and mouth of the wearer but does not press against the face. This type of protective device is particularly important to dentists. The drilling devices which are used by dentists spray liquid which mixes with matter in the mouth. Some of this mixture flies out of the patient's mouth to the dentist and is inhaled by the dentist. Some of this material also enters the eyes of the dentist.

There is a growing concern by dentists of being exposed to many types of germs and viruses which are found in saliva and blood; hepatitis and AIDS in particular. There is also a growing concern by dental patients and the need for protection from dentists and other physicians since these medical people are in contact with other patients who may have communicable diseases.

In view of the increased awareness by both physicians and patients of the dangers of disease transmission and of the need for protection, it is preferred by both patients and physicians to have the physician use a new sterile shield for each patient. As desirable as this is from a safety standpoint, it adds to the already growing cost of medical care. The relatively bulky nature of the shield also creates a storage problem since a large number of shields would have to be made available. These and other difficulties experienced with the prior art devices have been obviated in a novel manner by the present invention.

It is, therefore, a principal object of the invention to provide a low-cost medical face shield which can be discarded after one use.

A further object of the present invention is the provision of a low-cost medical face shield in which a large number of shields can be stored in a relatively compact stack.

A still further object of the invention is the provision of a medical face shield which is simple in construction and which is easy to use by the physician.

With these and other objects in view, as will be apparent to those skilled in the art, the invention resides in the combination of parts set forth in the specification and covered by the claims appended hereto.

SUMMARY OF THE INVENTION

The invention consists of a face shield to protect an individual against inhaling germs and other foreign bodies and comprises a clip which is adapted to hook on to the nose piece of a pair of eyeglasses and a contoured sheet of substantially rigid material which is removably attached to the clip so that the sheet can be removed and discarded and replaced by an identical sheet. When the sheet is attached to the clip, it lies in front of the nose and mouth of the individual.

BRIEF DESCRIPTION OF THE DRAWINGS

The character of the invention, however, may be best understood by reference to one of its structural forms, as illustrated by the accompanying drawings in which.

DESCRIPTION OF THE PREFERRED EMBODIMENT

Figure 1:
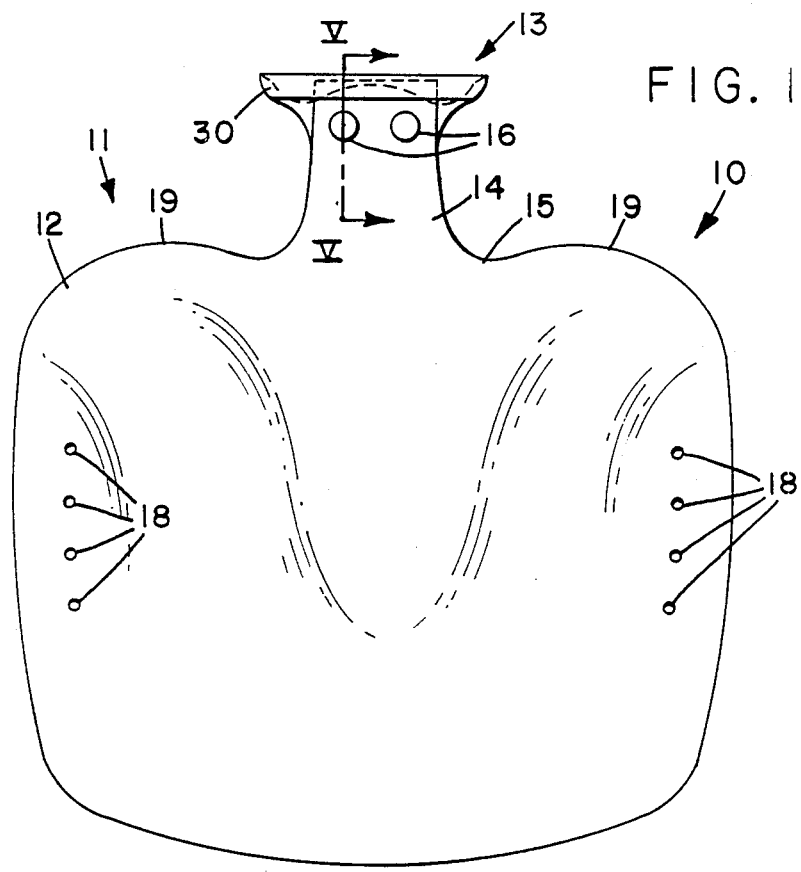
FIG. 1 is a front elevational view of a face shield embodying the principals of the present invention.
Figure 3:
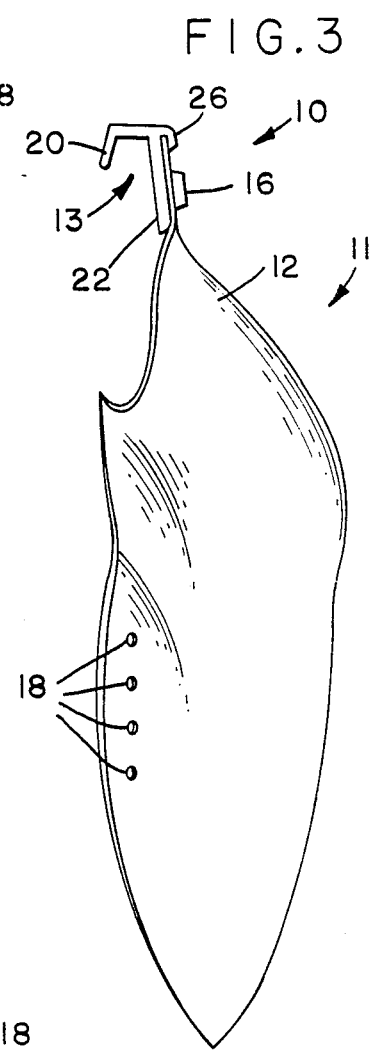
FIG. 3 is a left-side elevational view of the face shield.
Figure 2:
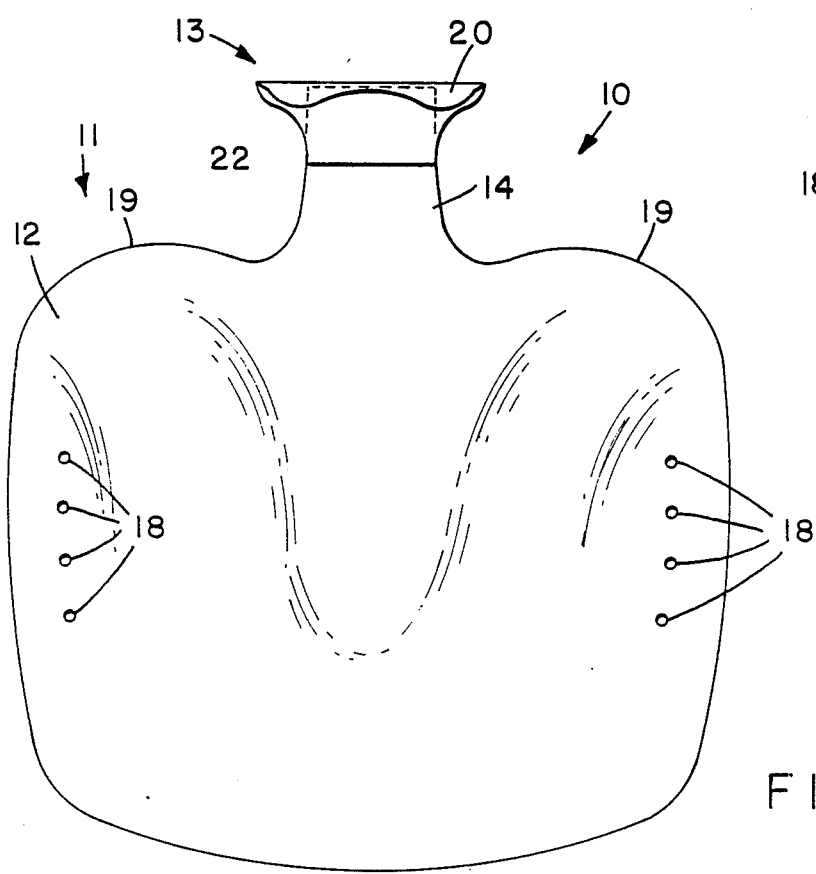
FIG. 2 is a rear elevational view of the face shield.

Referring first to FIGS. 1-3, the face shield of the present invention is generally indicated by the reference numeral 10 and comprises an expendable sheet portion which is generally indicated by the reference numeral 11 and a clip portion which is generally indicated by the reference numeral 13. The sheet portion 11, comprises a broad contoured rigid plastic sheet 12 and a tab 14 which extends upwardly from the top edge 15 of the sheet 12. The tab 14 has a top edge 27 and a pair of circular blisters 16. The sheet 12 also has a plurality of vent holes 18 adjacent each side edge of the sheet. The top edge 15 has an upwardly curved bulge 19 on each side of the tab 15 for a purpose to be described. The sheet 12 is preferably made of a relatively thin transparent plastic material.

Figure 5:
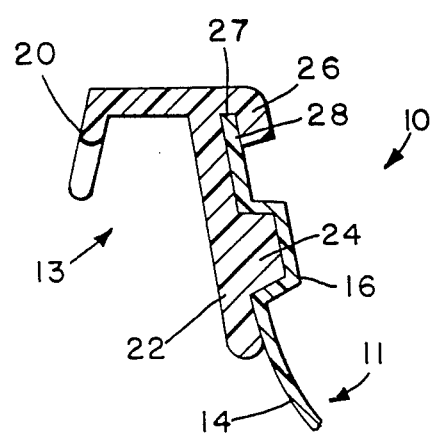
FIG. 5 is a fragmentary vertical cross-sectional view taken along the line V—V of FIG. 1.
Figure 7:
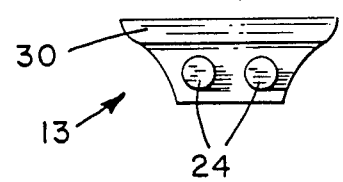
FIG. 7 is a front elevational view of the permanent clip portion of the face shield.
Figure 8:
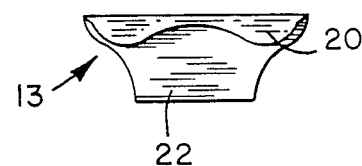
FIG. 8 is a rear elevational view of the clip portion.

Referring also to FIGS. 5-8, the clip portion 13 comprises a rearwardly-extending hook shaped flange 20 and a downwardly extending front flange 22. The front flange 22 has a pair of circular projections 24 which are adapted to fit into the blisters 16 of the sheet 12 in a snap fit. The clip portion 13 also includes a projection 26 at the top front edge of the clip which has a downwardly facing slot 28 for receiving the top edge 27 of the flange 14 as shown in FIG. 5.

Figure 4:
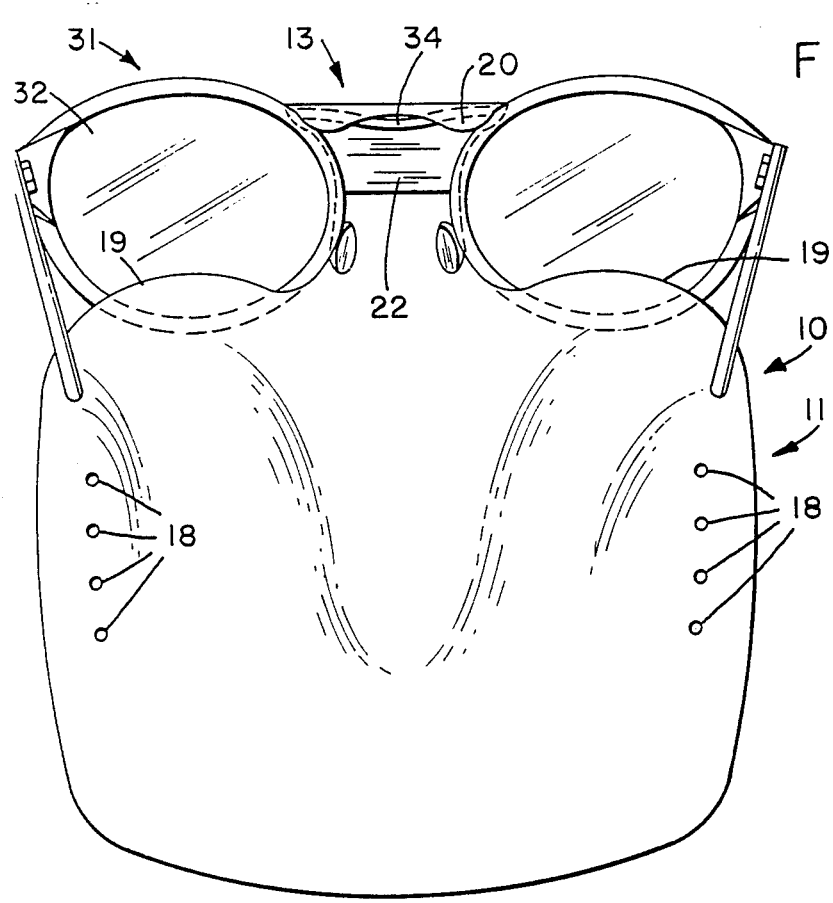
FIG. 4 is a rear elevational view of the face shield shown attached to a pair of eyeglasses.
Figure 6:
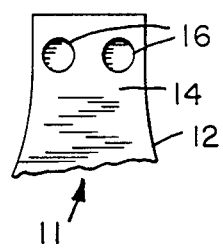
FIG. 6 is a rear elevational view of the disposable portion of the face shield, with portions broken away.

Referring particularly to FIGS. 4 and 5, the face shield 10 of the present invention is utilized in conjunction with a pair of conventional eyeglasses, generally indicated by the reference numeral 31, see FIG. 4. The projections 24 and the blisters 16 as well as the slot 28, constitute attaching means for attaching the sheet portion 11 to the clip portion 13. The sheet portion 11 is attached to the clip portion 13 by inserting the top edge 27 of the tab 14 into the slot 28 and snapping the blisters 16 over the projections 24 as shown in FIG. 5. The bulges 19 of the top edge 15 of the sheet 11 are placed behind the glass portions 32 of the eyeglasses 31 and the hook-shaped flange 20 is inserted over the bridge portion 34 of the eyeglasses as shown in FIG. 4. This maintains the face shield 10 securely mounted to the eyeglasses 31 so that when the eyeglasses are worn by the physician, the sheet portion 12 lies in front of the physician's face in front of the nose and mouth. The sheet 12 is shaped so that it rests against the bridge of the nose, thereby maintaining a space between the nostrils and the mouth of the physician. The holes 18 provide ventilation to the air space which is formed between the sheet 12 and the physician's face. After the physician has finished treating the patient, the sheet portion 11 is disconnected from the clip portion 13 and discarded. Prior to treating the next patient, the physician attaches a new sheet portion 11 to the clip portion 13 as described above. The clip portion 13 is a permanent part of the face shield 10 and is constructed of a much sturdier plastic than the sheet portion 11. The flange 22 is at least twice as thick sheet portion 11 and, preferably, approximately three times as thick as the sheet portion. The supply of expendable sheet portions 11 are conveniently nested together into a compact stack. Each sheet is individually wrapped in a sterile condition within a wrapper.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A face shield to protect an individual against inhaling germs and other foreign bodies, comprising:
   (a) a sheet of substantially rigid material having a lower portion which has a width which is substantially equal to the width of a conventional pair of eyeglasses and an upper edge and a tab which extends upwardly from a mid-point of said upper edge, said tab being substantially narrower than said lower portion,
   (b) a clip having a rearwardly extending hook-shaped flange for removably mounting the clip on the nosepiece of a pair of eyeglasses, said clip having a downwardly extending flange which extends in front of said nosepiece, and
   (c) mounting means for removably attaching said tab to said downwardly extending flange so that said sheet lies in front of the nose and mouth of the individual and substantially below at least a major portion of the lenses of the eyeglasses and said tab is substantially between the lenses of the eyeglasses.

2. A face shield as recited in claim 1, wherein said mounting means comprises:
   (a) a forwardly extending protrusion on said downwardly extending flange, and
   (b) a rearwardly facing cavity on said tab for receiving said protrusion in a snap fit.

3. A face shield as recited in claim 1, wherein said sheet is made of a transparent plastic.

4. A face shield as recited in claim 3 wherein said clip is made of transparent plastic.

5. A face shield as recited in claim 4, wherein said sheet is substantially thinner in cross-section than said clip.

6. A face shield as recited in claim 5, wherein said flange is at least twice as thick as said sheet.

7. A face shield as recited in claim 6, wherein said flange is approximately three times as thick as said sheet.

8. A face shield as recited in claim 1, wherein the upper edge of the lower portion of the sheet has an upwardly curving bulge behind the lower portion of each lense of the eyeglasses, each of said bulges being spaced from said tab.

9. A face shield to protect an individual against inhaling germs, and other foreign bodies, comprising:
   (a) a sheet of substantially rigid material having an upper edge and a tab which extends upwardly from a mid-point of said upper edge, said tab having a top edge,
   (b) a clip having a rearwardly extending hook-shaped flange for removably mounting the clip on the nosepiece of a pair of eyeglasses, said clip having a downwardly extending flange which extends in front of said nosepiece, and
   (c) mounting means for removably attaching said tab to said downwardly extending flange so that said sheet lies in front of the nose and mouth of the individual, said mounting means comprising a forwardly extending projection which has a downwardly facing vertical slot for receiving the top edge of said tab.

10. A face shield as recited in claim 9, wherein said upper edge has an upwardly curving bulge behind each lens of the eyeglasses, each of said bulges being spaced from said tab.

* * * * *